US011412949B2

(12) United States Patent
Paul et al.

(10) Patent No.: US 11,412,949 B2
(45) Date of Patent: Aug. 16, 2022

(54) MAGNETIC RESONANCE APPARATUS AND METHOD FOR CREATING A MAXIMUM INTENSITY PROJECTION

(71) Applicant: Siemens Healthcare GmbH, Erlangen (DE)

(72) Inventors: Dominik Paul, Bubenreuth (DE); Flavio Carinci, Erlangen (DE); Wilhelm Horger, Schwaig (DE)

(73) Assignee: Siemens Healthcare GmbH, Erlangen (DE)

( * ) Notice: Subject to any disclaimer, the term of this patent is extended or adjusted under 35 U.S.C. 154(b) by 309 days.

(21) Appl. No.: 15/934,293

(22) Filed: Mar. 23, 2018

(65) Prior Publication Data
US 2018/0271398 A1 Sep. 27, 2018

(30) Foreign Application Priority Data
Mar. 24, 2017 (DE) .......................... 102017205057.8

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0044* (2013.01); *G01R 33/34* (2013.01); *G01R 33/4835* (2013.01); *G01R 33/5608* (2013.01); *G01R 33/56509* (2013.01); *G01R 33/546* (2013.01); *G01R 33/5635* (2013.01)

(58) Field of Classification Search
CPC .... G01R 33/561; G01R 33/56; G01R 33/565; G01R 33/54; G01R 33/4833; G01R 33/4835; G01R 33/546; G01R 33/5608; G01R 33/34; G01R 33/5635; G01R 33/56509; A61B 5/0044; A61B 5/055; A61B 5/00
See application file for complete search history.

(56) References Cited

U.S. PATENT DOCUMENTS 6,144,201 A * 11/2000 Miyazaki ........... G01R 33/5673
324/306
6,411,088 B1 6/2002 Kuth et al.
(Continued)

FOREIGN PATENT DOCUMENTS

| CN | 1568893 A | 1/2005 |
| CN | 101887109 A | 11/2010 |
| CN | 105919593 A | 9/2016 |

OTHER PUBLICATIONS

Schaible. et al.: "Stellenwert selektiver MIP-Rekonstruktionen einer atemgetriggerten 3D-TSE-MR-Cholangiographie an einer Workstation gegenüber den MIP-Standardprojektionen und einer Single-Shot-MRCP";: Fortschr Röntgenstr; vol. 173; pp. 416-423; (2001).
(Continued)

*Primary Examiner* — Jermele M Hollington
*Assistant Examiner* — Suresh K Rajaputra
(74) *Attorney, Agent, or Firm* — Banner & Witcoff Ltd.

(57) ABSTRACT

In a method and magnetic resonance (MR) apparatus for creating a maximum intensity projection of a volume of an examination subject, MR data are acquired for a number of slices of the volume, and an MR image is reconstructed for each of the slices that MR data have acquired in order to create a maximum intensity projection for each of the slices. The maximum intensity projection of the respective slice is shown on a display. The slices, which have a thickness of at least 15 mm, have various slice directions, in order to display the maximum intensity projections from various directions.

9 Claims, 3 Drawing Sheets

(51) Int. Cl.
    *G01R 33/34*     (2006.01)
    *G01R 33/56*     (2006.01)
    *G01R 33/565*     (2006.01)
    *G01R 33/483*     (2006.01)
    G01R 33/563     (2006.01)
    G01R 33/54     (2006.01)

(56) References Cited

U.S. PATENT DOCUMENTS

| | | | |
|---|---|---|---|
| 2002/0032376 A1* | 3/2002 | Miyazaki | A61B 6/541 600/410 |
| 2007/0106149 A1* | 5/2007 | Mistretta | G01R 33/56325 600/410 |
| 2010/0289493 A1 | 11/2010 | Stemmer | |
| 2018/0271398 A1 | 9/2018 | Paul et al. | |

OTHER PUBLICATIONS

Minov et al.: "MR Cholangiopancreatography—positioning, parameters and technical advances"; European Society of Radiology; pp. 1-17; (2012).
Jingjing, Shi et al;"RSNA 2013—Central Nervous System Image Science"; Radiology Practice; vol. 29; No. 1; pp. 6-11; Jan. 2014.
Office Action dated Mar. 4, 2020 for Chinese Patent Application No. 201810233582.6.
Chinese Office Action dated Aug. 25, 2020 for Chinese Application No. 201810233582.6.

\* cited by examiner

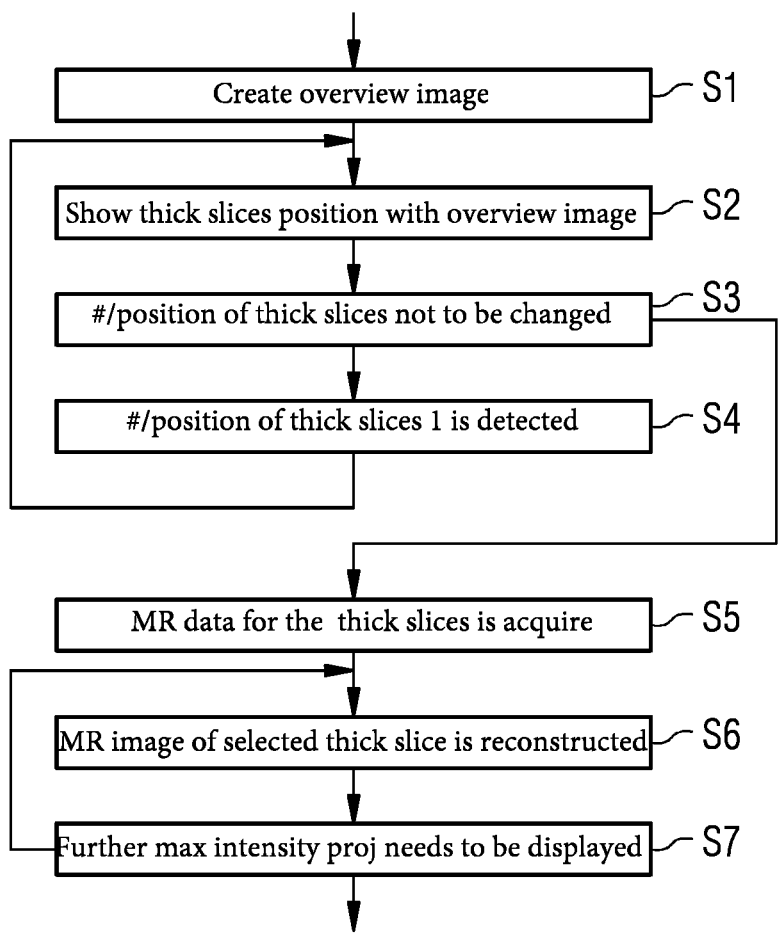

MAGNETIC RESONANCE APPARATUS AND METHOD FOR CREATING A MAXIMUM INTENSITY PROJECTION

BACKGROUND OF THE INVENTION

Field of the Invention

The present invention concerns a method and a magnetic resonance apparatus for creating a maximum intensity projection using the magnetic resonance system.

Description of the Prior Art

Magnetic resonance cholangiopancreatography (MRCP) is a non-invasive method for imaging the (fluid-filled) hepatobiliary system (the bile duct system and the main efferent ducts of the pancreas) by the use of magnetic resonance tomography. For this purpose, according to the prior art, high-resolution T2-weighted three-dimensional imaging with a very long echo time is carried out, with maximum intensity projections being created from various angles of view (known as radial views) for the diagnosis.

Due to the large volume of data, which cannot be acquired in one breath hold, according to the prior art the data must be acquired over a fairly long period (longer than one breath hold) so that the patient has to hold his or her breath a number of times. Due to movement between the breaths, or due to a changing breathing pattern, the MR data that are acquired in different breath holds is not always acquired with the patient at the same position. Therefore, there is often inconsistent MR data, which then leads in the reconstruction of the image data to what are known as ghosts and/or fuzzy MR images. In the worst case scenario, the MR images generated according to the prior art can be classed as unusable for diagnosis, which then requires a fresh data acquisition, which lasts 6 to 10 minutes, or even leads to the patient being given a new appointment. Accordingly, the resulting additional costs are high.

SUMMARY OF THE INVENTION

An object of the present invention is to provide a method and apparatus for creating a maximum intensity projection, wherein the problems described above at least do not arise with the same as they occur in the prior art.

The method according to the invention creates a maximum intensity projection of a volume section of an examination object using a magnetic resonance system as follows.

MR data from a number of thick slices of the volume section with the magnetic resonance apparatus. The various thick slices, each of which has a slice thickness of at least 15 mm and at most 20 mm, have various slice directions.

An MR image is reconstructed for each thick slice using the MR data acquired in the manner above. The MR images that have been reconstructed in this way each form a maximum intensity projection for the respective thick slice. In other words, each reconstructed MR image represents the maximum intensity projection for the respective thick slice.

Each maximum intensity projection of the respective thick slice is shown on a display of the magnetic resonance system. In this step, an operator (for instance, the physician providing treatment) can have in particular one of the previously created maximum intensity projections shown on the display. It is possible for an operator to change to one of the previously created maximum intensity projections and show this on the display in order to look at the volume section that is to be examined from a different viewing direction. It is further possible at the same time to show a number of the previously created maximum intensity projections on the display.

Instead of the three-dimensional data acquisition known from the prior art, a two-dimensional thick slice imaging is carried out. With the respective thick slice image, a projection of the entire slice thickness is achieved onto a plane, which therefore corresponds to a maximum intensity projection.

Since the acquisition of the MR data for one of these thick slices is clearly faster compared with three-dimensional data acquisition according to the prior art, the MR data for a thick slice can advantageously be acquired in one breath hold. Nevertheless, it is also possible for the MR data to be acquired in a triggered manner with the patient breathing freely.

It still remains possible for the MR data for various thick slices to be acquired at different positions if, for example, a movement has occurred between two breath holds. Nevertheless, since according to the invention the MR data for the one breath hold are reconstructed into one MR image, and the MR data for another breath hold are reconstructed into a different MR image, the effects of a movement between the two breath holds are less than in the three-dimensional data acquisition according to the prior art. In other words, according to the invention, the movement between the two breath holds advantageously leads only to a movement between the two reconstructed MR images, whereas according to the prior art, the movement negatively influences the overall reconstructed three-dimensional MR imaging.

Depending on the number of thick slices from which MR data are to be acquired, the data acquisition can also be carried out in one breath hold (approximately 25 seconds).

The volume section from which each maximum intensity projection is created includes at least part of the hepatobiliary system of the examination subject, such that the method according to the invention can be used for MR cholangiopancreatography.

According to a preferred embodiment of the invention, the MR data are acquired with an echo time of at least 400 ms (and usually no more than 800 ms).

Using a very long echo time advantageously ensures that only one fluid provides a signal.

To acquire the MR data, conventional turbo spin echo sequences or HASTE ("Half-Fourier Acquisition Single-shot Turbo spin Echo") sequences can be used.

Furthermore, T2 preparation can be used in the MR data acquisition.

In a spin echo sequence, a 180° refocusing pulse is applied for T2 preparation after detecting the echo signal, which pulse is followed by a 90° pulse at the refocusing point of the following echo signal. This combination of RF pulses flips the transverse magnetization back into the longitudinal direction. Since the longitudinal magnetization is given a "kick start" by this, it acquires a higher value at the point when the next excitation pulse is applied. This results in a greater transverse magnetization, which then advantageously allows a shorter TR time ("Time to Repetition") and hence a faster data acquisition.

According to a further preferred embodiment of the present invention, the thick slices for which MR data are acquired have a common axis of rotation. This axis of rotation is located centrally in each thick slice and is therefore perpendicular to the slice direction of each slice. Here the axis of rotation in particular is the same distance away from the upper surface and from the lower surface of each respective thick slice on which the slice vector is perpendicular, and is the same distance from the two lateral surfaces of the respective thick slices, which the axis of rotation does not intersect.

This embodiment allows the physician conducting the examination to turn the respective maximum intensity projection that is to be displayed around this axis of rotation in order, as a result, to look at the volume section from a different viewing direction in each case.

Here, a planned position of each thick slice can be displayed together with an overview image of an anatomy of the examination subject in the volume section. Starting from the number and the planned position of the thick slices, the physician conducting the examination can determine afresh the number of thick slices and the respective planned position of the thick slices. It is possible for only the position of the thick slices to be changed, but for the number thereof to remain unchanged. It is also possible, however, for a (planned) thick slice to be removed, as a result of which the number is reduced accordingly, or for a further thick slice to be added as a (planned) thick slice, including the position thereof. With the use of the overview image with the respective display of the planned position of the thick slices that are to be acquired, the number of thick slices to be acquired and each planned position of the thick slices to be acquired is determined according to the invention. The steps of acquiring the MR data, reconstructing the respective MR images, and displaying the maximum intensity projection for each slice are carried out according to the previously determined number and the planned position of the thick slices.

Because the position of the thick slices to be acquired is displayed in the volume section together with the overview image of the anatomy of the examination subject, the physician conducting the examination can advantageously be very precisely informed as to which region of the volume section is acquired with the respective thick slice.

The thick slices can also be displayed as overlapping rectangles together with the common axis of rotation of the thick slices. In this variant, the operator virtually looks at the thick slices in the direction of the axis of rotation.

By rotation around the axis of rotation, each of the thick slices displayed can be merged into any other of the thick slices. This applies to each embodiment with an axis of rotation.

However, in a different variant only one of the thick slices is displayed in the form of a rectangle, together with a circle and the axis of rotation. On the circle, at least for each thick slice that is not currently displayed, there is a marking from which the physician conducting the examination can derive the position of the respective thick slice that is not shown. The center of the circle corresponds to the axis of rotation, such that the axis of rotation is perpendicular to the circle's surface.

In both variants, the axis of rotation can be located centrally in the field of view (FOV). Nevertheless, it is also possible for the axis of rotation to be arranged so as to be offset from the center of the field of view. According to the invention, it is also possible for the user to alternate between the two display variants.

In the last variant described, it is also possible according to the invention for an action relating to one of the markings that is to be carried out (for example, selection of the respective marking) to be determined. Depending on this action, it is then possible, instead of displaying the thick slice that has just been displayed, for the thick slice that corresponds to the marking to be displayed, together with the overview image, the circle, the axis of rotation and the markings.

As a result, the physician conducting the examination can check the position of each or of certain planned thick slices, by causing each or certain planned thick slices to be displayed as a result of the action.

With the previously described embodiments, the operator receives a very good overview as to which thick slices are intended to be acquired according to the invention. The operator thus has the opportunity to change the number of planned thick slices and/or the position of the planned thick slices, as long as the planned thick slices have the same axis of rotation or merge together due to a rotation around the circle.

The present invention also encompasses a magnetic resonance apparatus designed to create a maximum intensity projection of a volume section of an examination subject. The magnetic resonance apparatus includes an RF controller, a gradient controller and an image sequence controller, which are designed to acquire the MR data for a number of thick slices. Furthermore, a computer of the magnetic resonance apparatus is designed to reconstruct MR images on the basis of the acquired MR data, in order to create a maximum intensity projection on the basis of these MR images for each of the thick slices. The magnetic resonance apparatus has a display monitor at which the computer causes the maximum intensity projection to be displayed. The thick slices have various slice directions, such that the maximum intensity projections are created for various viewing directions.

The advantages of the magnetic resonance apparatus according to the invention correspond to the advantages of the method according to the invention, as described above.

The present invention also encompasses a non-transitory electronically readable data storage medium, such as a DVD, a magnetic tape, a hard drive or a USB stick, on which electronically readable control data, in particular software (see above), are stored. When this control data (software) are read from the data carrier and stored in a computer of a magnetic resonance apparatus, all the embodiments of the method according to the invention that are described above can be carried out.

In addition to faster data acquisition compared with conventional three-dimensional data acquisition, the present invention has the advantage that the MR images created and hence the maximum intensity projections have fewer artifacts caused by a movement during data acquisition. Consequently, according to the invention, more stable MR images and hence maximum intensity projections are created, allowing a better diagnosis.

BRIEF DESCRIPTION OF THE DRAWINGS

FIG. 4 is a flowchart of the method according to the invention for creating maximum intensity projections.

DESCRIPTION OF THE PREFERRED EMBODIMENTS

Figure 1:
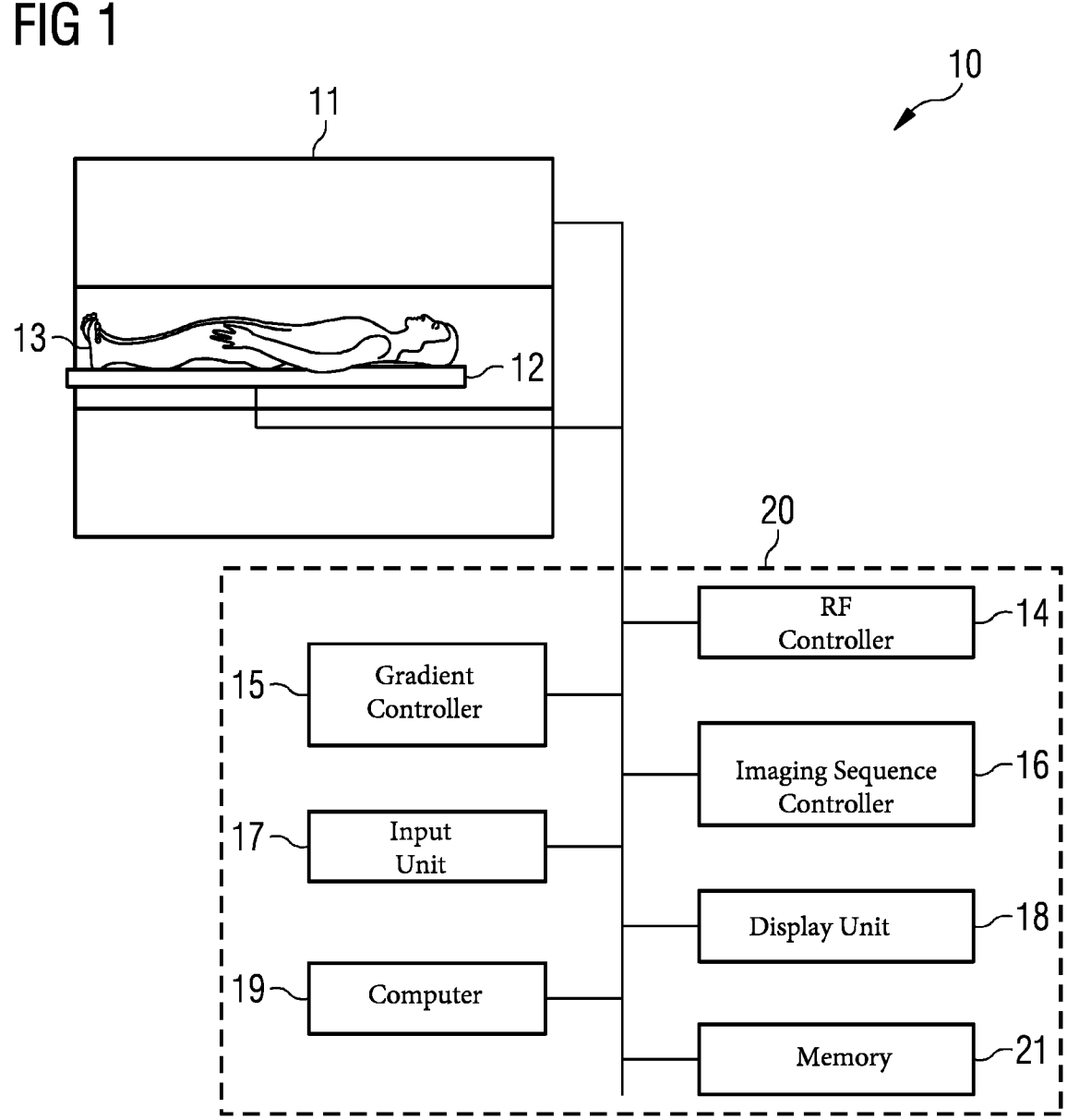
FIG. 1 schematically illustrates a magnetic resonance apparatus according to the invention, with which maximum intensity projections according to the invention of a volume of an examination subject are generated.

FIG. 1 illustrates a magnetic resonance apparatus with which MR data for an examination subject 13 are acquired. The magnetic resonance apparatus 10 has a scanner 11 that has a basic field magnet that generates a polarization field BO, wherein an examination subject 13, on a bed 12 is moved into the scanner 11, in order to record spatially encoded magnetic resonance signals there from the examination subject 13. The coils used for signal recording, such as a whole body coil or local coils, are not shown, for clarity. The invention can be used in what is known as parallel imaging, in which the MR signals are recorded at the same time by a number of local coils, a coil array of local coils. By applying radio-frequency pulses and activating magnetic field gradients, the magnetization generated by the polarization field BO can be deflected from the equilibrium state, as the magnetization returns to the equilibrium state, and the resulting magnetization are spatially encoded and are detected by the receiving coils. How MR images can be generated by applying RF pulses and by activating on magnetic field gradients in various combinations and sequences is known to those of ordinary skill in the art, and thus need not be explained in further detail herein.

The magnetic resonance apparatus 10 further has a control computer 20 that controls the magnetic resonance apparatus 10. The control computer 20 includes a gradient controller 15 to control and activate the necessary magnetic field gradients. An RF controller 14 is provided to control and to generate the RF pulses to deflect the magnetization. An imaging sequence controller 16 controls the sequence of the magnetic field gradients and RF pulses and hence indirectly controls the gradient controller 15 and the RF controller 14. An operator can control the magnetic resonance apparatus by entering data via an input unit 17, and on a display unit 18 MR images, maximum intensity projections, and other data necessary for control, can be displayed. A computer 19 with at least one processor (not shown) is provided to control the various components in the control computer 20. Furthermore, a memory 21 is provided in which, for example, program modules or programs can be stored, which, when run by the computer 19 or by the processor, can control the running of the magnetic resonance apparatus. The computer 19 is, as explained below, designed to calculate the MR images acquired from the MR data and hence the maximum intensity projections according to the invention.

Figure 2:
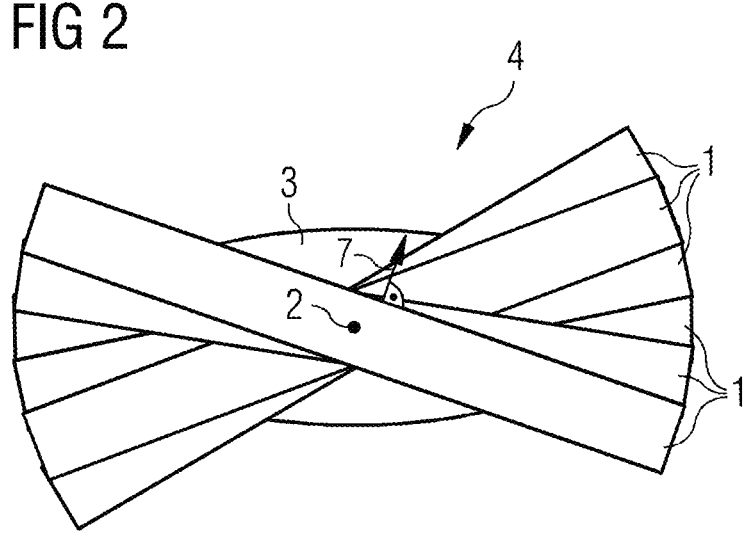
FIG. 2 shows the planned thick slices according to the invention as rectangles having a common axis of rotation with an anatomy of the examination subject.

FIG. 2 shows the planned thick slices 1 according to the invention, together with a common axis of rotation 2 over an anatomy 3 of the examination subject in an overview image 4. It can be seen that each thick slice can be merged into any other of the thick slices shown 1 by an appropriate turn round the axis of rotation 2. Since the thick slices 1 therefore differ from one another only in respect of the angle of rotation, all the planned thick slices 1 have a different slice direction 7.

With the overview image 4 shown in FIG. 2, the user (for example, the physician operating the magnetic resonance system) is given an overview as to which maximum intensity projections according to the invention are being created.

Figure 3:
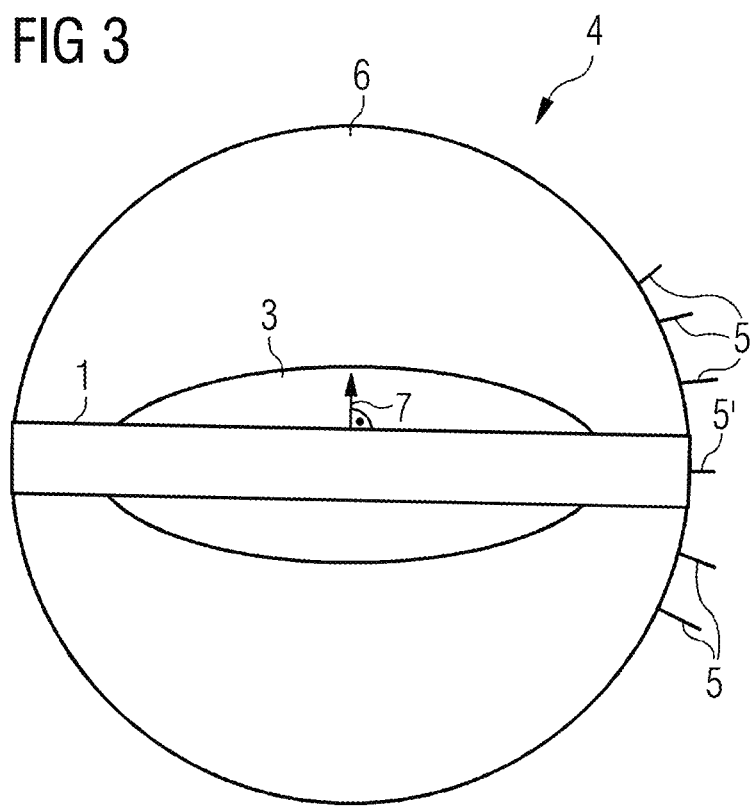
FIG. 3 shows one of the planned thick slices according to the invention as a rectangle together with markings showing the further planned rectangles over an anatomy of the examination subject.

A similar overview image 4 according to the invention is shown in FIG. 3. In the embodiment shown in FIG. 3, only one planned thick slice 1 is shown over the anatomy 3 of the examination subject. In addition, for each further planned thick slice 1, a marking 5 is shown on a circle 6. The central point in the circle 6 corresponds to the common axis of rotation 2 of the planned slices 1. The marking 5, 5' denotes in particular the point in the circle 6 at which a central axis of the respective thick slice 1, which is projected into the circular plane and runs perpendicular to the slice direction 7 and to the axis of rotation 2, intersects the circle 6.

For instance, by clicking on the relevant marking 5, the thick slice 1 that relates to the marking 5 can be displayed in the form of a rectangle instead of the thick slice 1 shown in FIG. 3. Likewise, the overview image 4 according to the invention that is shown in FIG. 3 gives the user a good overview as to from which thick slices 1 each maximum intensity projection will be created. By moving the markings 5 on the circle, the projection angle of the respective maximum intensity projection can be changed. Furthermore, by deleting and/or adding markings 5', 5, the number of planned thick slices 1 and hence indirectly also the duration of the data acquisition can be adjusted to suit the relevant requirements.

FIG. 4 shows a flowchart of an embodiment according to the invention.

In step S1 an overview image of the hepatobiliary system of the examination subject 13 is created in order to show in step S2 the position of the planned thick slices 1 together with the overview image 4. If in step S3 the number and/or the position of the planned thick slices 1 are not to be changed, the method jumps to step S5. If the result of the questions in step S3 is that the number and/or the position of the planned thick slices 1 needs to be changed, the change in the number and/or the position of the planned thick slices 1 is detected in step S4 and the method reverts to step S2.

In step S5, the MR data for the planned thick slices is acquired and in step S6 an MR image of a thick slice 1 selected by the user is reconstructed using the acquired MR data and with this the maximum intensity projection for the selected thick slice 1 is created and displayed. If the result of the questions in step S7 is that a further maximum intensity projection still needs to be displayed, the method reverts to step S6.

It is also possible according to the invention for the reconstruction of the MR images to be started as soon as the MR data for the respective thick slice has been acquired. In this variant, step S6 would include only the displaying of the MR image that relates to the selected thick slice, which relates to the maximum intensity projection of the selected thick slice.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for creating a maximum intensity projection of a volume of an examination subject, comprising:
   with a control computer, operating a magnetic resonance (MR) data acquisition scanner in order to execute a computer-controlled acquisition of MR data from a plurality of two-dimensional slices in image space of a volume of an examination subject, wherein said plurality of two-dimensional slices have a common axis of rotation, which intersects each slice centrally, perpendicular to said slice direction of the respective slice, and each slice has a slice thickness of at least 15 mm;
   providing the acquired MR data to a reconstruction computer and, in said reconstruction computer, executing a reconstruction algorithm in order to reconstruct an MR image for each of said two-dimensional slices from said MR data in image space, the respective two-dimensional slices having different slice directions in image space, and producing a maximum intensity projection for each of said two-dimensional slices in the respective slice directions; and providing said maximum intensity projections for each of said slices to a display screen and displaying the respective maximum intensity projections of the respective slices at said display screen, with the different slice directions of the respective slices causing the maximum intensity projections to be presented at said display screen from said different directions.

2. A method as claimed in claim 1 comprising operating said MR data acquisition scanner in order to execute said computer-controller acquisition of said MR data with an echo time that is larger than 400 ms.

3. A method as claimed in claim 1 comprising operating said MR data acquisition scanner in order to execute said computer-controlled acquisition of said MR data with T2 preparation.

4. A method as claimed in claim 1 comprising:
with said computer, operating said MR data acquisition scanner to execute a computer-controlled acquisition of an overview image of the examination subject;
in said computer, executing a planning procedure wherein said slices are superimposed at respective planned positions on the volume of the examination subject in the overview image;
in said computer, starting from said planned positions of said slices, determining a number of said slices and a new planned position of said number of said slices; and
operating said MR data acquisition scanner to acquire said MR data from said number of said slices at said new planned positions of said slices, and reconstructing the MR images and displaying the maximum intensity projections according to said number and said newly planned positions of said slices.

5. A method as claimed in claim 4 comprising displaying the planned positions of each of said slices together with said overview image at said display screen, with said slices being represented at said display screen as overlapping rectangles situated around a common axis of rotation that intersects each slice centrally perpendicular to the respective slice direction of the respective slice.

6. A method as claimed in claim 4 comprising, in said computer, executing a planning procedure in which each of said slices is displayed superimposed on said volume of the examination subject in said overview image, with only one of said slices being presented as a rectangle together with a circle, around which said slices rotate with one axis of rotation that is common to all of the slices, said one axis of rotation intersecting each slice centrally perpendicularly to the slice direction of the respective slice, and displaying a marking on said circle for each slice that is not displayed, but is planned.

7. A method as claimed in claim 6 comprising, in said computer, determining an action to be taken dependent on said marking and, dependent on said action, displaying only one slice that relates to said marking, together with said overview image, said circle, said axis of rotation and said marking.

8. A magnetic resonance (MR) apparatus comprising:
an MR data acquisition scanner;
a control computer configured to operate said MR data acquisition scanner in order to execute a computer-controlled acquisition of MR data from a plurality of two-dimensional slices in image space of a volume of an examination subject, wherein said plurality of two-dimensional slices have a common axis of rotation, which intersects each slice centrally, perpendicular to said slice direction of the respective slice, and each slice has a slice thickness of at least 15 mm;
a reconstruction computer configured to execute a reconstruction algorithm in order to reconstruct an MR image for each of said two-dimensional slices from said MR data in image space, the respective two-dimensional slices having different slice directions in image space, and to produce a maximum intensity projection for each of said two-dimensional slices in the respective slice directions; and
said reconstruction computer being configured to provide said maximum intensity projections for each of said slices to a display screen and to display the respective maximum intensity projections of the respective slices at said display screen, with the different slice directions of the respective slices causing the maximum intensity projections to be presented at said display screen from said different directions.

9. A non-transitory, computer-readable data storage medium encoded with programming instructions, said storage medium being loaded into a computer system of the MR apparatus, said computer system comprising a control computer and a reconstruction computer, and said programming instructions causing said computer system to:
operate a magnetic resonance (MR) data acquisition scanner in order to execute a computer-controlled acquisition of MR data from a plurality of two-dimensional slices in image space of a volume of an examination subject, wherein said plurality of two-dimensional slices have a common axis of rotation, which intersects each slice centrally, perpendicular to said slice direction of the respective slice, and each slice has a slice thickness of at least 15 m;
execute a reconstruction algorithm in order to reconstruct an MR image for each of said two-dimensional slices from said MR data, the respective two-dimensional slices having different slice directions in image space, and producing a maximum intensity projection for each of said two-dimensional slices in the respective slice directions; and
display the respective maximum intensity projections of the respective slices at a display screen, with the different slice directions of the respective slices causing the maximum intensity projections to be presented at said display screen from said different directions.

* * * * *